United States Patent [19]

Desecki et al.

[11] Patent Number: 4,929,242
[45] Date of Patent: May 29, 1990

[54] SOLUTION AND METHOD FOR MAINTAINING PATENCY OF A CATHETER

[75] Inventors: Vince C. Desecki, Ingelside; Michael R. Prisco, Aurora, both of Ill.

[73] Assignee: Baxter International Inc., Deerfield, Ill.

[21] Appl. No.: 349,948

[22] Filed: May 8, 1989

Related U.S. Application Data

[63] Continuation of Ser. No. 935,655, Nov. 26, 1986, abandoned.

[51] Int. Cl.$^5$ .............................................. A61M 5/325
[52] U.S. Cl. ...................................... 604/266; 604/50
[58] Field of Search .............. 604/266, 269, 400, 50, 604/187, 29, 403, 101, 51, 675; 424/101

[56] References Cited

U.S. PATENT DOCUMENTS

| | | | |
|---|---|---|---|
| 3,874,384 | 4/1975 | Deindoerfer et al. | 604/408 |
| 3,916,892 | 11/1975 | Latham, Jr. | 604/269 |
| 3,951,148 | 4/1976 | Herb | 604/408 |
| 3,963,026 | 6/1976 | Herb | 604/408 |
| 4,190,057 | 2/1980 | Hill et al. | 128/675 |
| 4,258,723 | 3/1981 | McCue et al. | 604/50 |
| 4,301,153 | 11/1981 | Rosenberg | 424/101 |
| 4,339,433 | 7/1982 | Kartinos et al. | 604/29 |
| 4,432,750 | 2/1984 | Estep | 604/403 |
| 4,464,167 | 8/1984 | Schoendorfer et al. | 604/6 |
| 4,479,799 | 10/1984 | Thiel | 604/187 |
| 4,595,021 | 7/1986 | Shimizu et al. | 604/266 |
| 4,601,697 | 7/1986 | Mammolenti et al. | 604/269 |
| 4,666,427 | 5/1987 | Larsson et al. | 604/51 |
| 4,680,177 | 7/1987 | Gray et al. | 424/101 |

*Primary Examiner*—C. Fred Rosenbaum
*Assistant Examiner*—Kathleen A. Daley
*Attorney, Agent, or Firm*—Paul C. Flattery; Mary R. Jankowsky; Amy L. H. Rockwell

[57] ABSTRACT

A solution is described that can be used to maintain the patency of an I.V. catheter or other vascular access device having a lumen. The density and osmolarity of the solution are adjusted so that the density and osmolarity of the solution are approximately equal to the density and osmolarity of whole blood in a patient. The solution can be injected into the lumen of the vascular access device to prevent blood from the patient from entering the lumen.

4 Claims, 3 Drawing Sheets

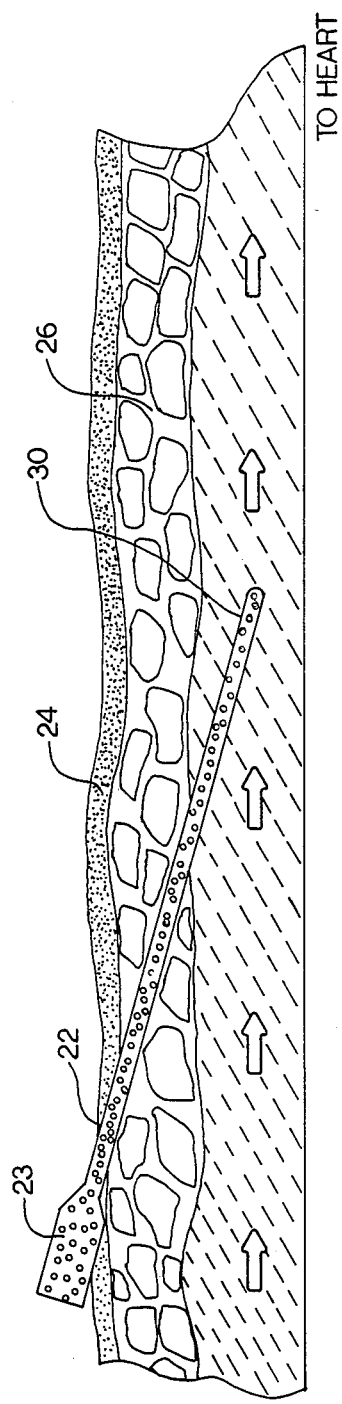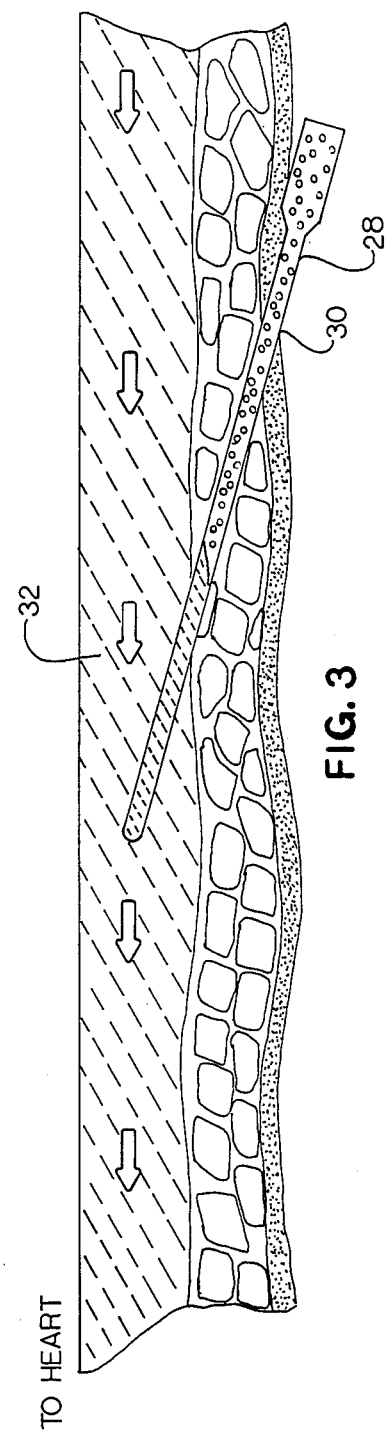

4,929,242

SOLUTION AND METHOD FOR MAINTAINING PATENCY OF A CATHETER

This application is a continuation of application Ser. No. 06/935,655, filed Nov. 26, 1986 now abandoned.

BACKGROUND OF THE INVENTION

The invention generally relates to solutions and methods for maintaining the patency of a vascular access device having a lumen and more specifically relates to density-adjusted solutions and the use of such solutions in which the density of the solution is approximately equal to the density of whole blood.

Traditionally, intravenous (I.V.) therapy has been given in a continuous mode. In recent years, for both cost and clinical benefit, methods of intermittent I.V. therapy have been used. In these cases, a catheter or other vascular access device remains in a patient's body continuously, but is periodically detached from traditional I.V. tubing. An anticoagulant combined with a carrier solution is injected into the lumen of the catheter to maintain the patency of the catheter by preventing blood clots from forming in the catheter while it is disconnected from the I.V. tubing.

A typical catheter flush procedure that is used with intermittent I.V. therapy is described below. After proper placement in a patient of a vascular device, such as a catheter, a rubber septum or injection site is attached to the catheter hub permitting ease of access to the catheter lumen without compromising the sterile fluid path. This arrangement is commonly referred to as a "heparin lock".

After the medication has been administered, the catheter injection site assembly is typically flushed with an inert isotonic solution such as physiologic sodium chloride (saline solution). This is done to minimize potential incompatibility problems between the intravenous drug previously administered through the catheter, and the anticoagulant in the carrier solution to be administered.

Traditionally, sodium heparin derived from either pork intestinal mucosa or bovine lung tissue in concentrated strengths of from 1 to 100 units per milliliter in a carrier solution of physiologic saline is administered to the catheter. Flushing volumes of the anticoagulant generally exceed the internal volume of the vascular device to insure total flush. The anticoagulent is administered on an intermittent basis, dependent on the modality of drug therapy, although generally given every eight hours, but not to exceed 24 hours. In this way, it is thought that should blood enter the lumen of the vascular device, the coagulation process will be retarded by the existence of the anticoagulant; thus permitting the catheter to remain patent even when it is in use only on an intermittent basis.

Heparin lock I.V. therapy has experienced significant growth since 1980. Increased clinical popularity can be linked to the following benefits associated with the use of heparin locks: (1) increased ambulatory freedom for patients; (2) general cost containment; and (3) clinical benefits of fluid restriction. Each of these benefits is discussed in greater detail below.

First, normal continuous I.V. therapy requires the patient to remain attached to an intravenous set solution container and I.V. pole. A heparin lock allows the patient to be disconnected from this apparatus, thereby greatly increasing the mobility of the patient.

Second, the use of heparin locks or intermittent drug therapy has been shown to significantly reduce costs. This is due to the fact that simpler intravenous administration sets or syringes can be used to administer drugs through a heparin lock as opposed to more complicated intravenous administration sets designed to be used with multiple containers. Yet another cost savings associated with the use of heparin locks is a reduction in nursing time required to monitor the flow of an I.V. set on a continuous basis as required in more traditional therapies. Yet, another cost savings associated with the use of heparin locks is the complete elimination of the use of pumps or other electrical or mechanical flow control devices to maintain fluid flow through a catheter on a continuous basis.

Third, the use of heparin locks has clinical popularity in patients in which fluid restriction is desired. Oftentimes, intravenous access is required in patients that do not necessarily need intravenous solution or require limited volumes of solution. For example, patients with high blood pressure or other circulatory problems may actually tolerate only limited fluid intake. Traditional continuous I.V. therapy required one liter or more solution per day to maintain catheter patency. A heparin lock completely eliminates the need for continuous fluid administration.

In 1984, approximately 20 million heparin lock procedures were conducted in the U.S. This represents 24% of the total 85 million cannulations given during the same period. Considering a conservative treatment regiment, a cumulative total of 300 million saline heparin flushes were administered during that period. Statistics have indicated a 10% growth rate per year in heparin lock therapy. Over the next ten years, it is estimated that from one-third to one-half of all I.V. therapy will be given by heparin lock.

A great deal has been written in the literature regarding the problem of clot prevention within the lumen of peripheral and central indwelling catheters. Traditionally, extremely low dosing of heparin anticoagulants flushed through the catheter lumen on an intermittent basis has been an effective retardant to clot development in most clinical cases. Nonetheless, as high as 12% of all intermittent sites established continue to be lost due to coagulation buildup and eventual lumen blockage. Attempts to counteract this problem by increasing the dosage, strength, and/or the frequency of administration have not necessarily yielded improved clinical results. In contrast, the risk exists that higher heparin concentrations, volumes or more frequent administrations could increase the likelihood of drug incompatibility reactions with the heparin or, to a much lesser extent, systemic effects on internal physiologic coagulation patterns.

It is important to understand certain fluid dynamic and physiologic factors affecting the initiation of the coagulation cascade in a vascular lumen in a patient, particularly as they relate to the occasional inability to maintain catheter patency regardless of the small heparin dosing schedule used. Assurance of a higher percentage of catheter lumen clear passage could have significant, positive clinical benefit while also affording new options to the development of an antiblocking clot catheter.

To varying degrees based on individual patient hematologic chemistry, fibrinogen layering and, to a lesser extent, platelet aggregation, begin simultaneously with blood entry into the catheter lumen. This is the first stage of the coagulation process. Unfortunately, backflow of blood into the catheter during venipuncture is fundamental to establishing final catheter placement and even though the bulk of the blood is removed by a flushing solution, some fibrinogen layering may have occurred. Subsequent establishment of a minimum fluid flow, or of a static heparin column, serves to retard the chemical reaction between prothrombin and the pre-established fibrinogen layer creating thrombin and the fibrin monomer which eventually polymerizes into clot formation.

In view of the foregoing problems associated with heparin locks, the invention described herein represents an improvement over the traditional use of anticoagulant solutions to maintain the patency of a catheter.

SUMMARY OF THE INVENTION

It is an object of the invention to provide a solution for maintaining the patency of a catheter during intermittent drug therapy administration.

It is a further object of the invention to provide a solution having density adjusted so that the density of the solution is approximately equal to the density of whole blood in a patient.

It is an object of the invention to provide a solution having osmolarity approximately equal to the osmolarity of whole blood.

It is yet another object of the invention to provide a solution for maintaining the patency of a catheter that does not necessarily require the use of an anticoagulant.

The invention can be summarized as a solution for minimizing blood entry from a patient into a vascular access device having a lumen in which the solution has a density substantially equal to whole blood. In some embodiments, the solution contains a density-adjusting portion and a carrier. The density-adjusting portion may be taken from the group consisting of glycerol, a protein-based colloidal substance, dextrose, dextran, hespan, and sodium chloride. The carrier may be water. In yet other embodiments of the invention, an anticoagulant may be added to the solution taken from the group consisting of sodium heparin, hirudin, warfarin and citrates. In yet other embodiments of the invention, the solution may include an osmolarity-adjusting portion taken from the group consisting of glycerol, dextrose, and sodium chloride.

BRIEF DESCRIPTION OF THE DRAWINGS

FIG. 1 depicts a catheter inserted into a vein in which the catheter flush solution is in a desired "solution over blood" position;

FIG. 3 depicts a catheter inserted into a vein in which the catheter flush solutions is an undesired "blood over solution" position.

DETAILED DESCRIPTION OF THE PREFERRED EMBODIMENT

Figure 2B:
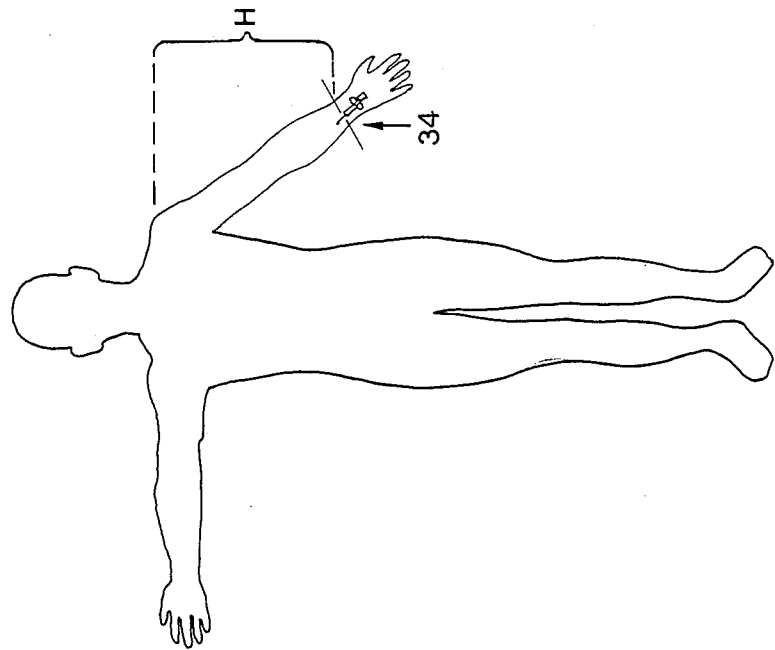
FIGS. 2 (a) and (b) depict typical patient movement which creates an unfavorable "blood over solution" position.

Several factors affect the continued efficacy of the static heparin column. These include: (1) blood velocity; (2) positive pressure differential; (3) diffusion of heparin solution into the bloodstream; (4) positional variability of the intravenous catheter site related to the presence of compressible air within the catheter system; and (5) positional variability of the intravenous catheter site related to density displacement of heparin solution by whole blood.

The invention is based on the concept that the primary factor causing 12% of the intermittent catheter sites to be lost is that orienting the catheter in the blood-over solution position causes the denser blood to displace the less dense traditional heparin solution from the catheter lumen, causing blood coagulation development within the lumen of an indwelling catheter. In other words, by adjusting the density of the solution to be injected into the lumen of a vascular device so that the density of the solution is substantially equal to the density of whole blood, the average length of patency of the lumen of a vascular access device can be greatly enhanced. Of the five factors listed above relating to the efficacy of a static heparined column, investigative testing has found the use of a density adjusted solution to significantly reduce the extent of blood ingress into a vascular device. Although other independent variables such as positive pressure differential, positional variability related to the presence of compressible air and concentration diffusion also may impact the extent of blood ingress, it is believed these independent variables have substantially less impact than the concept of density adjusting the flush solution.

The common schematic view of a heparin lock device installed in a patient is as pictured in FIG. 1. This can be referred to as the "solution-over-blood" orientation. As can be seen in this figure, a catheter 22 is inserted through the subcutaneous layer 24 of a patient and into a vein 26. Heparin or other anticoagulent solution 28 fills the internal lumen 30 of the catheter 22. The arrangement illustrated in FIG. 1 is a favorable arrangement because the less dense heparin solution 28 is positioned above the more dense whole blood 32 of the patient. This arrangement typically occurs when a patient is in the supine position with a catheter located on the upper portion of the patient's hands, arms, or torso.

Figure 2A:
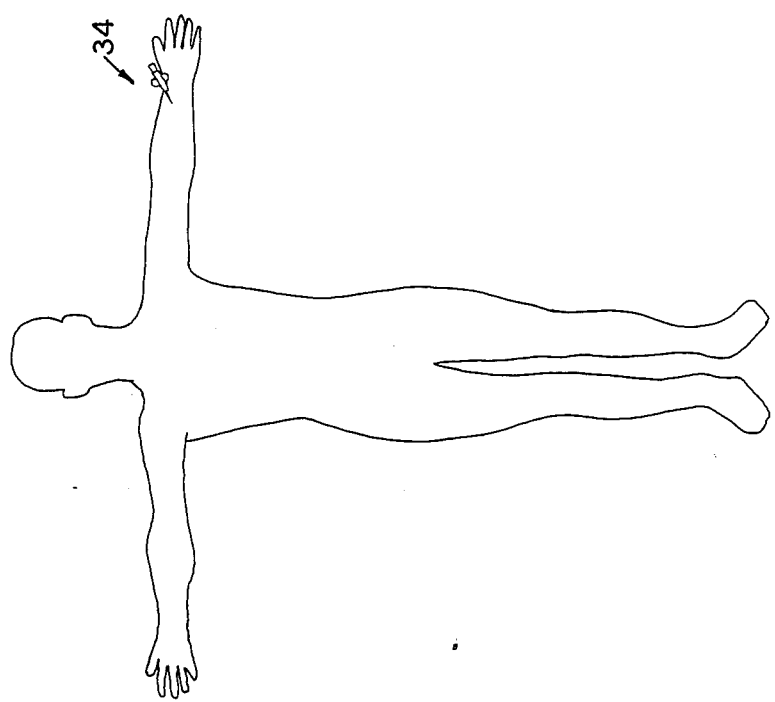

However, a "blood-over-solution" orientation which is considered the unfavorable position is also possible when a patient has positioned himself so that the catheter is located on the lower portion of the patient's hands, arms, or torso as seen in FIGS. 2 (a) and (b). In addition to the development of a blood-over-solution orientation, lowering the catheter site designed by 34, a distance "H" as illustrated in FIG. 2 (b) causes a slight pressure increase directed toward the catheter solution column.

However, in the presence of air entrapped within the catheter assembly, hydrostatic pressure changes can cause blood ingress into the catheter regardless of solution density. In the case of "blood-over-solution" orientations, use of less dense traditional anticoagulants permit an ingress of blood into the lumen of the vascular device, thus allowing blood clots to form in the catheter and increasing the possibility that the patency of the catheter may be lost. In the case of density adjusted flush solutions, measurable reductions in the rate of blood ingress into the lumen of the catheter have been observed.

FIG. 3 depicts unfavorable catheter position whereby the more dense blood 32 is over the less dense anticoagulant solution 28. This condition is unstable since the denser blood will settle to the bottom of the catheter lumen 30 displacing the anticoagulent solution. It is precisely this effect which is hypothesized to drain solution from an intermittent IV-lock catheter when the blood-over-solution orientation is achieved. As a practical matter, the blood-over-solution orientation occurs frequently in a patient using a heparin lock. For instance, whenever the patient lowers his extremity as illustrated in FIG. 3 (b), or even rolls over in bed so that the arm containing the intermittent I.V. lock is below the medial plane of his body. This invention seeks to overcome this problem in a novel way by using a density-adjusted solution to reduce migration of blood into the lumen of the catheter.

In view of the fact that a major object of the invention is to provide a solution which has a density substantially equal to that of whole blood, it was necessary to determine the range of densities that components of whole blood can have under various conditions. The range of blood component densities has been found to span from 1.0266 to 1.0962 g/ml. Specifically, this range is depicted by nominal plasma density at 1.0266 and nominal red cell density at 1.0962 g/ml. Slight changes in density approximately plus or minus 0.5% have been documented as a result of temperature changes from ambient (room temperature) to elevated body temperature. Therefore, density-adjusted solutions for use within the body will be slightly different than density-adjusted solutions for in vitro use.

The density of human blood is also affected by the hematocrit level in a particular patient. For example, a pediatric patient tends to have slightly higher whole-blood density, such as 1.0638 g/ml. plus 0.0050, minus 0.0081) compared to the density of adult male whole blood which is 1.058 (plus or minus 0.006 g/ml). Therefore, in one embodiment of the invention, the density of the solution can be adjusted to more closely match the density of the particular type of patient for which the solution is to be used. However, in the broadest terms in accordance with the invention, the density of the solution may range from 1.0266 to 1.0962 g/ml. This range is based on the range of density of the individual blood components. In a more preferred embodiment of the invention, the density of the solution may range from 1.055 to 1.06 g/ml. This range is based on the high end of the normal blood density range in a patient at 37° C. Such a patient may be a pediatric or an adult patient with relatively dense blood, and hermatocrit levels ranging from 48% to 56%. In another preferred embodiment of the invention, the density of the solution may range from 1.0253 to 1.0638 g/ml. This range is typical of the normal range of whole blood density at 37° C. having hermatocrit of from 38% to 53%.

Although the density of the solution is considered to be the most important factor in the efficacy of the solution, another relevant variable to the efficacy of the solution is the viscosity of the solution as compared to the viscosity of whole blood. The viscosity is important because it affects the sedimentation rates of blood into the intravenous catheter lumen while in the unfavorable blood-over-solution position. In one embodiment of the invention, the minimum relative viscosity of the solution is 1.08 centipoise at 37° C. relative to plasma viscosity of 37° C., which is 1.18 to 1.59 centipoise based on in-vitro determinations.

In the preferred embodiment of the invention, the relative viscosity of the solution may range from 1.00 to 10.0 centipoise at 37° C. In accordance with the invention, it is desired to have the viscosity of the solution to be higher than the normal relative viscosity of whole blood. This is because the sedimentation rates of the red blood cell will be reduced by using a solution having a higher viscosity as well as matched density to that of whole blood.

As noted above, the solution may have both density-adjusting and osmolarity-adjusting portions added to the carrier. The following table is supplied to illustrate the dominant effect of various possible additives.

| DENSITY AND OSMOLARITY EFFECTS OF VARIOUS CATHETER FLUSH SOLUTION ADDITIVES | | |
|---|---|---|
| SOLUTION ADDITIVE | DENSITY ADJUSTER | OSMOLARITY ADJUSTER |
| Glycerol | X | X |
| Protein Based Colloidial Substance (i.e. Albumin) | X | |
| Dextrose | X | X |
| Dextran | X | |
| Hespan | X | |
| Sodium Chloride | X | X |

In the preferred embodiment, the solution may also include an osmolarity adjusting portion to adjust the osmolarity of the solution so that it is substantially equal so that it is substantially equal to the osmolarity of whole blood. The relative amount of each of the density and osmolarity adjusting portion and carrier used can be computed based on the following two equations for aqueous solutions with an arbitrary number of additives.

The solution density may be calculated according to:

$$\rho_{sol}(T) = \frac{V_w \rho_w(T) + \sum_{i=1}^{n} m_i}{V_w + \sum_{i=1}^{n} \frac{m_i}{\rho_i}} \quad [\text{eq. 1}]$$

Where:

| Symbols | Subscripts |
|---|---|
| m = mass | 1 = additive 1 |
| $\rho$ = density | 2 = additive 2 |
| V = volume | i = additive i |
| Os = osmolarity | w = water |
| MW = molecular weight | sol = solution |
| $\alpha$ = dissociation factor | |
| T = temperature | |
| n = total number of additives | |

While the osmolarity of the solution may be calculated according to:

$$Os = \frac{\sum_{i=1}^{n} \frac{m_i \alpha_i}{MW_i}}{V_w + \sum_{i=1}^{n} \frac{m_i}{\rho_i}} \quad [\text{eq. 2}]$$

The previous two equations presume that: (1) the solution volume equals the sum of the volumes before mixing; (2) the temperature dependance of solution density is primarily attributable to that of water; and (3) the dissociation factors are taken to be the theoretical upper limits.

The simultaneous solution of the previous two equations using standard mathematical techniques will give the formulation of a solution having a specified density and osmolarity. It should be noted that the previous two equations are solvable for only two variables, $m_1$ and $m_2$. If more than two additives are to be included in the formulation, the amounts of additional species, $m_3-m_n$, must be specified according to other criteria.

The following table illustrates the use of the above equations to generate a variety of solutions having a given osmolarity and densities which vary in incremental steps of 0.002 g/ml. In the table illustrated below, three additives were used. These additives are sodium chloride, albumin, and glycerol. The amount of glycerol was specified to be 25 grams.

DENSITY OF SOLUTIONS
OSMOLARITY = 310.0 mOsm/L

| MOL. WT. | MOL. WT. | DENSITY (g/ml) | DISSOC FACTOR |
|---|---|---|---|
| ADDITIVE 1 NACL | 58.44 | 2.1650 | 2.00 |
| ADDITIVE 2 ALBUMIN | 66000 00 | 1.3640 | 1.00 |
| ADDITIVE 3 GLYCEROL | 92.10 | 1.2599 | 1.00 |

| | SOLUTION DENSITY (g/ml) | WATER (ml) | SOLUTION VOLUME (ml) |
|---|---|---|---|
| 1 | 1.05000 | 1000.0 | 1169.8 |
| 2 | 1.05200 | 1000.0 | 1177.2 |
| 3 | 1.05400 | 1000.0 | 1184.8 |
| 4 | 1.05600 | 1000.0 | 1192.4 |
| 5 | 1.05800 | 1000.0 | 1200.1 |
| 6 | 1.06000 | 1000.0 | 1207.9 |
| 7 | 1.06200 | 1000.0 | 1215.8 |
| 8 | 1.06400 | 1000.0 | 1223.9 |
| 9 | 1.06600 | 1000.0 | 1232.0 |

| GRAMS OF ADDITIVES PER 1000 ml WATER | | | CONC OF ADDITIVES IN FINAL SOLUTION (w/v %) | | |
|---|---|---|---|---|---|
| 1 | 2 | 3 | 1 | 2 | 3 |
| 2.58 | 202.95 | 25.00 | .220 | 17.349 | 2.137 |
| 2.64 | 213.04 | 25.00 | .224 | 18.096 | 2.124 |
| 2.70 | 223.26 | 25.00 | .228 | 18.844 | 2.110 |
| 2.77 | 233.60 | 25.00 | .232 | 19.591 | 2.097 |
| 2.83 | 244.08 | 25.00 | .236 | 20.339 | 2.083 |
| 2.90 | 254.70 | 25.00 | .240 | 21.086 | 2.070 |
| 2.96 | 265.46 | 25.00 | .244 | 21.834 | 2.056 |
| 3.03 | 276.36 | 25.00 | .248 | 22.581 | 2.043 |
| 3.10 | 287.40 | 25.00 | .252 | 23.328 | 2.029 |

Typical solutions described by this invention use water as a carrier. The invention, however, is not intended to exclude nonaqueous solutions. Therefore, in calculating the amount of each additive for a given solution, a typical approach is to use the temperature of water as the only temperature considered in those instances in which all the other additives are in the solid state prior to forming the solution. In those instances in which one or more of the additives is a liquid (such as glycerol), the temperature of the liquid additive will also be taken into consideration.

In an embodiment of the invention, the density-adjusting portion of the solution can be taken from the group consisting of glycerol, a protein-based colloidal substance, dextrose, dextran, sodium chloride and hespan. The osmolarity adjusting portion can be taken from the group consisting of glycerol, dextrose, and sodium chloride. The carrier is water in the preferred embodiment. Further, an anticoagulant may be added taken from the group consisting of sodium heparin, hirudin, warfarin as citrates. As discussed above, the proportion of each of these solutions used may be varied in accordance with the equations discussed above to produce a solution that is density and osmolarity adjusted to be substantially equal to that of whole blood. In the preferred embodiment, the solution is isotonic.

However, in other embodiments, the solution may be hypertonic or hypotonic.

Although it is clear that a variety of combinations and concentrations can be used to produce the desired results in accordance with the invention, one embodiment of the invention envisions that a solution formed of 100 ml. of water to which is added approximately 23.87 grams of glycerol and approximately 900 mg. of NaCl per 100 ml. solution may be used. In another embodiment of the invention, solution may be formed of water to which is added approximately 16.90 grams of glycerol, 900 mg. NaCL, and approximately 4.02 grams dextrose powder per 100 ml. solution. Both of the above combinations are hypertonic in nature in relation to the relative isotonic nature of the whole blood. This hypertonic nature has not been considered to be clinically unacceptable.

In yet another embodiment of the invention; various isotonic solutions have also been considered. For example, the solution may be formed of 100 ml. water, and approximately 15.09 grams. dextrose powder. Various other combinations of components and portions may be used in yet other embodiments of the invention. For example, a solution may be formed of 100 ml. water to which is added approximately 8.56 grams dextran having an average molecular weight ranging from 25,000 to 125,000, and approximately 5.47 grams dextrose powder. In still yet another embodiment of the invention, the solution may be formed of 100 ml. of water to which is added approximately 9.86 grams dextran having an average molecular weight ranging from 10,000 to 80,000, and approximately 5.45 grams dextrose powder. In some embodiments of the invention, the solution may be an isotonic, protein-based colloidal substance such as biologic albumin. Examples of such solutions include 100 ml. of water and approximately 18.53 grams biologic albumin and approximately 0.883 mg. sodium chloride.

In further embodiments, starch-based solutions can be used such as a solution formed of hespan and dextrose solution.

It is important to recognize that an anticoagulant is not required in order for the invention to perform its function. In some instances, an anticoagulant may even be contraindicated. For example, patients with hemophilia or other blood disorders may react very unfavorably to anticoagulants and thus, may not be candidates for heparin lock therapy. However, to any of the above solution combinations, an anticoagulant may, or may not, be added. Any known biologically compatible anticoagulant may be used, such as sodium heparin, hirudin, warfarin and citrates. Although an anticoagulant is not necessary to the operation of the invention, an anticoagulant may enhance the effectiveness of the solution. If an anticoagulant such as sodium heparin is used, a range of from 10 to 100 units of anticoagulant per ml density adjusted solution is envisioned.

While a variety of solutions have been discussed above, specific solutions have been evaluated in vitro models. These solutions are discussed below by way of example.

The procedure used for evaluating solutions in vitro can be described as follows. Actual densitometer readings were taken on three solution samples previously theoretically calculated. The solutions were: (1) 1,000 ml. water plus 186.7 grams dextrose; (2) 1,000 ml 0.9% saline, plus 384.3 grams glycerol; and (3) 1,000 ml. 0.9% saline, plus 90 grams dextrose, plus 202.1 grams glycerol. These formulations were physically measured using a traditional densitometer for density verification. Actual density measurements were found to be (1) 1.0598; (2) 1.0696; and (3) 1.0683 respectively for each of the solutions listed above.

A test technique was established to determine the extent of interfacial mix 36 (FIG. 4) between density-adjusted solution 38 and bovine blood 40 previously adjusted to approximately 45 hermatocrit in an in vitro environment. Micropipette hermatocrit glass tubes 42 equal in internal diameter to the internal diameter of specific commonly used peripheral catheters were chosen. In one group, glass pipettes having an internal diameter of from 0.045 to 0.050 were used. This diameter is equal to the lumen diameter of 16 gauge catheter tubing. In another group, glass pipettes having an internal diameter of from 0.030 to 0.035 were used. This diameter is equal to the lumen diameter of 18-gauge catheter tubing.

Heparinized bovine blood 40 previously adjusted to 40 hermatocrit using crystaloid solution was utilized for testing purposes.

Figures 4A, 4B, 4C:
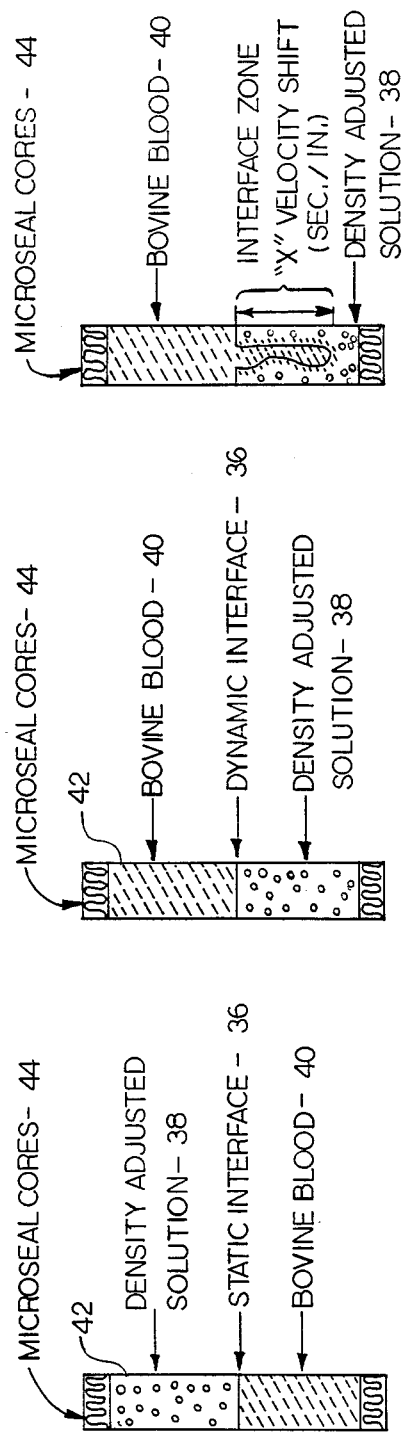
FIGS. 4 (a)-(c) depict various micro-hematocrit pipette configurations used in various in vitro tests of solutions in accordance with the invention.

Test procedure required 50% of pipette (42) as illustrated in FIG. 4(a) to be filled with bovine blood 40, and the remainder filled with density adjusted test solution 38. Pipettes were filled by a combination of capillary flow and vacuum draw. Pipette ends were sealed with microsealant 44. Care was taken to ensure compressible air was eliminated from each test column. Test pipettes were prepared and handled prior to measurement in a vertical orientation to ensure a solution over blood interface as illustrated in FIG. 4(a). It was observed that in this orientation, visible solution fall-out, displacement, or sedimentation into the blood column did not occur initially. This indicated that, in fact, the blood was of a heavier density than the solution.

Test manipulation consisted of controlled 180° inversion as illustrated in FIG. 4(b) of filled microcapillary glass pipettes 42 so that the bovine blood column 40 previously below the density adjusted solution 38 was now above the density adjusted solution 38. A stop watch was used to measure the velocity in time by which the blood was able to fall into the density adjusted solution portion of the column. This distinction was visibly very clear and measurable as depicted in FIG. 4(c). In other words, the velocity of interface shift was measured in terms of seconds per inch. A positive control consisting of pipettes having a 50% blood column and a 50% column of traditional heparinized saline solution was used for comparative purposes. In the 16-gauge pipette study, the positive control revealed a mean of 4.76 seconds per inch. In the 18-gauge pipette study, the positive control revealed a mean of 6.28 seconds per inch. The mean combined value for the positive control test solution was 5.52 seconds per inch. A minimum of four replications per both positive control and test cases were conducted for each of the examples discussed below.

EXAMPLE 1

In the first solution tested which consisted of 1,000 ml. water plus 186.7 grams dextrose, the following results were obtained. In the 16-gauge pipette, a mean velocity interface of 24.49 seconds per inch was observed. In the 18-gauge pipette, a mean velocity interface of 34.97 seconds were observed. This compared favorably to a positive control which was observed having a mean velocity interface of 5.52 seconds per inch.

EXAMPLE 2

In a second solution consisting of 1000 ml. 0.9% saline plus 384.3 grams glycerol, the following results were obtained. In the 16-gauge pipette, a mean velocity interface of 26.48 seconds per inch was observed. In the 18-gauge pipette, a mean velocity interface of 36.06 seconds per inch was observed. This compared favorably to a positive control which was observed having a mean velocity interface of 5.52 seconds per inch.

EXAMPLE 3

In a third solution consisting of 1000 ml. 0.9% saline plus 90.0 grams dextrose plus 202.1 grams glycerol, the following results were obtained. In the 16-gauge pipette, a mean velocity interface of 21.50 seconds per inch was observed. In the 18-gauge pipette, a mean velocity interface of 33.58 seconds per inch was observed. This compared favorably to a positive control which was observed having a mean velocity interface of 5.52 seconds per inch.

Although the invention has been described and illustrated in detail, it is to be clearly understood that the same is by way of illustration and example only, and is not to be taken by way of limitation; the spirit and scope of this invention being limited only by the terms of the appended claims.

We claim:

1. A liquid for minimizing blood entry from a patient into a vascular access device, wherein said liquid has a density approximately equal to the density of whole blood of the patient and includes water, glycerol and NaCl in a proportion such that for each 100 ml of water the liquid includes approximately 23.87 grams of glycerol and approximately 900 mg of NaCl.

2. A liquid for minimizing blood entry from a patient into a vascular device, wherein said liquid has a density approximately equal to the density of whole blood in the patient and includes water, glycerol and NaCl in a proportion such that for each 100 ml of water, the liquid includes approximately 16.90 grams of glycerol, approximately 900 mg of NaCl, and approximately 4.02 grams of dextrose power.

3. A liquid for minimizing blood entry from a patient into a vascular access device, wherein said liquid has a density approximately equal to the density of whole blood in the patient and includes water, dextran and dextrose powder in a proportion such that for each 100 ml of water, the liquid includes approximately 8.56 grams of dextran having an average molecular weight from approximately 25,000 to 125,000 and approximately 5.47 grams of dextrose powder.

4. A liquid for minimizing blood entry from a patient into a vascular access device, wherein said liquid has a density approximately equal to the density of whole blood in the patient and includes water, dextran, and dextrose powder in a proportion such that for each 100 ml of water, the liquid includes approximately 9.86 grams of dextran having an average molecular weight from 10,000 to 80,000 and approximately 5.95 grams of dextrose powder.

* * * * *